US00PP18869P3

(12) United States Plant Patent
Duncan

(10) Patent No.: US PP18,869 P3
(45) Date of Patent: Jun. 3, 2008

(54) **SEASHORE *PASPALUM* PLANT NAMED 'SI 98'**

(50) Latin Name: *Paspalum vaginatum*
Varietal Denomination: SI 98

(75) Inventor: Ronny R. Duncan, Boerne, TX (US)

(73) Assignee: University of Georgia Research Foundation, Inc., Athens, GA (US)

( * ) Notice: Subject to any disclaimer, the term of this patent is extended or adjusted under 35 U.S.C. 154(b) by 14 days.

(21) Appl. No.: 11/254,056

(22) Filed: Oct. 19, 2005

(65) Prior Publication Data

US 2007/0089214 P1 Apr. 19, 2007

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para
(74) *Attorney, Agent, or Firm*—Greenlee Winner and Sullivan PC

(57) ABSTRACT

A new and distinct vegetatively reproduced cultivar of seashore papalum, *Paspalum vaginatum,* which is characterized by its semi-dwarf, low growing and rapidly spreading growth habit, its superior salt tolerance and its ability to maintain high turf density and quality at a range of mowing heights. These characteristics make it desirable for wall to wall use on golf courses, athletic fields and recreational venues where water quality is a consideration.

3 Drawing Sheets

Figure 1:
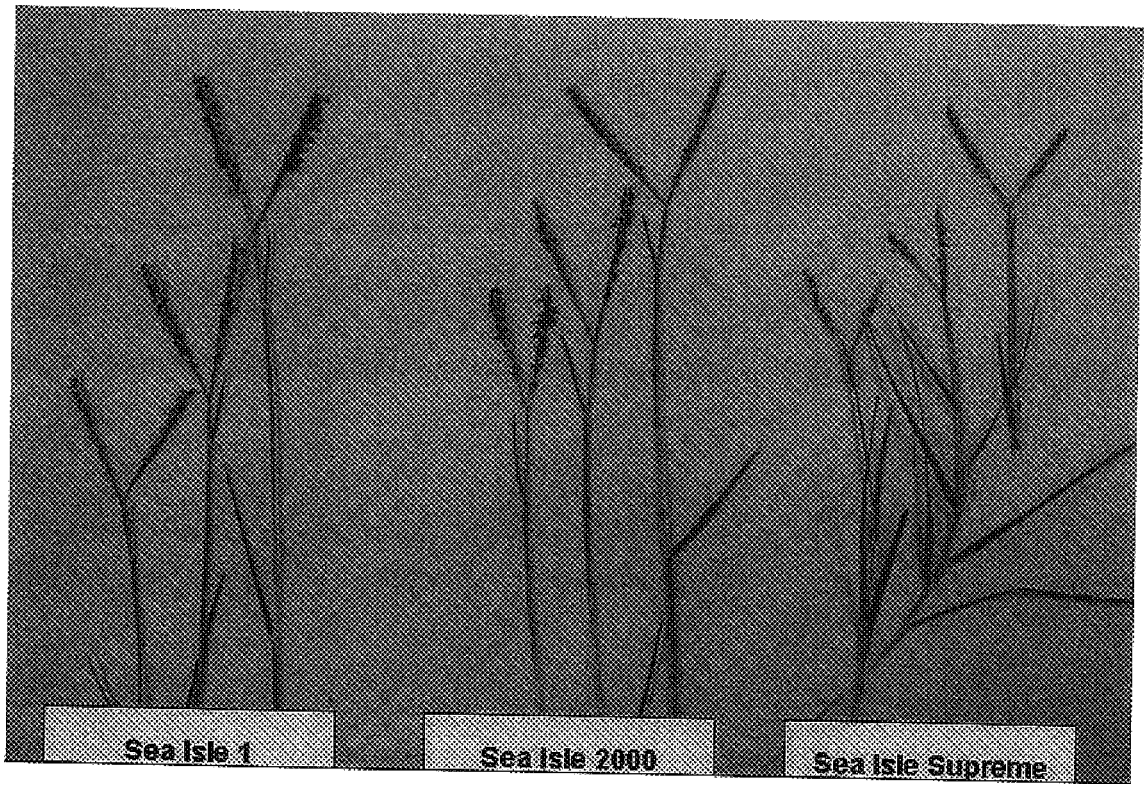

Botanical classification: *Paspalum vaginatum* O. Swartz
Varietal denomination: Seashore *paspalum* 'SI 98'.

BACKGROUND OF THE INVENTION

The present invention comprises a new and distinct cultivar of *Paspalum vaginatum,* commonly known as seashore *paspalum*, and hereafter referred to by the varietal denomination 'SI 98'.

*Paspalum vaginatum* is a grass in the Panicoideae subfamily that inherently colonizes saline ecosystem, e.g. along sea coasts and on brackish sands. It is an ecologically aggressive, littoral warm-season perennial grass species varying in leaf texture from very coarse to finer-leaf types with potential for use in recreational turf. It produces both rhizomes and stolons and can tolerate waterlogged conditions and periodic meso-saline flooding. The grass occurs in the wild in both hemispheres. In the Americas, it is found along the Atlantic, Gulf of Mexico, and Pacific coastlines in marshy, brackish ecosystems. Generally, *P. vaginatum* is a self-incompatible, diploid species with 20 chromosomes. *P. vaginatum* has been introduced into salt-affected areas as the need for forages, land reclamation and recreational turf have increased. With increasing pressures on golf course developers to use coastal venues and to irrigate with reclaimed or brackish low quality water sources, there is a need for a high-quality salt-tolerant seashore *paspalum* turfgrass with specific adaptations that allow its use course-wide on roughs, fairways, tees, and greens.

'SI 98' was selected from a world wide collection of 300 samples of seashore *paspalum* collected by the inventor, primarily from seashore *paspalum* plantings on golf courses as mutant variants in growth habit, leaf texture, and level of salt tolerance, having potential for improved turf type selections. The original samples were vegetatively propagated and evaluated first in the greenhouse at Griffin, Ga., and later expanded to field evaluations at Griffin under mowing heights ranging from 3/16" to 2". 'SI 98' was included in the NTEP Bermuda grass trial at Griffin established during 2002 and evaluated for turf quality and related characteristics during 2002–2004. 'SI 98' was established and evaluated to the Griffin greens and fairway plots during 2002–2004, and was included in replicated seashore *paspalum* turf evaluations established at Jay, Fla. in 2003 and in Griffin and Tifton, Ga. in 2004. The selection was also evaluated for suitability as a greens grass on two premier golf clubs in Florida and South Carolina for one year prior to this application.

SUMMARY OF THE INVENTION

The following characteristics have been consistently observed and, to the best knowledge of the inventor, their combination forms the unique characteristics of 'SI 98' as a new and distinct cultivar.

1) Low growing semi-dwarf growth habit that tolerates a wide range of mowing heights and still maintains good turf density and quality. This property makes 'SI 98' potentially attractive as a grass that can be used on all parts of the golf course, from roughs to fairways to tees to greens.
2) Extremely vigorous spreading growth habit for rapid establishment, grow-in and recovery from any maintenance challenges.
3) Exceptional high level of salt tolerance.

'SI 98' has been compared primarily to 'Sea Isle 2000' (U.S. Plant Pat. No. 12,625), a variety recently developed for greens use in the golf industry, and which, to the inventors knowledge is most similar to 'SI 98'. Comparative evaluations of the grasses grown in the greenhouse and in field research plots at Griffin, Ga. showed that 'SI 98' differed from 'Sea Isle 2000' in the following characteristics.

1) In replicated field research trials in 2004 at Tifton, Ga. and at Griffin, Ga., 'SI 98' produced 89% and 86% cover respectively compared to 56% and 74% cover by, 'Sea Isle 2000' during the same time frame, i.e. a more aggressive trait for establishment and initial grow-in. Color scores in full turf shoot density research plots for 'SI 98' were better at 6.0 and 8.2 respectively compared to 5.8 and 7.6 for 'Sea Isle 2000'.
2) In a replicated greenhouse experiment conducted in the Spring of 2004, 'SI 98' had much better "grow-in" rate than 'Sea Isle 2000'. After 67 days from sprigging at 20% coverage rate, 'SI 98' covered 95% and produced 14.3 g dry top growth biomass compared to 53% coverage and 5.9 g dry top growth biomass of 'Sea Isle 2000'.
3) In greenhouse experiments, 'SI 98' produced 2.7 g top growth and 4.5 g crown and root growth, for a total biomass of 7.9 g when grown in the presence of 40 $dSm^{-1}$ saline (ocean water is approximately 54 $dSm^{-1}$) compared to 1.6 g top growth, 3.1 g crown and root growth and 5.3 g total biomass of 'Sea Isle 2000' i.e., higher overall salinity tolerance. 'SI 98' had only 17.8% reduction in total biomass when compared to growth in fresh water, relative to 46.8% reduction in total biomass of 'Sea Isle 2000'.
4) 'SI 98' had many significant morphological differences from 'Sea Isle 2000'. The flag leaf of 'SI 98' is positioned closer to the spike branch, the flag leaf blade is longer and wider and the flag leaf sheath is shorter than that in 'Sea Isle 2000'. 'SI 98' has shorter leaf blades on flowering tillers and shorter and narrower leaf blades on stolons than those of 'Sea Isle 2000'. The 'SI 98' peduncle is shorter and thicker than that of 'Sea Isle 2000' and the unmowed culm height and seed head exsertion height of 'SI 98' are shorter than those of 'Sea Isle 2000.' The leaf color of 'SI 98' is slightly lighter green than that of 'Sea Isle 2000'. Because of the self-incompatible nature of this grass species, no seed set or subsequent seedling emergence has been observed in monostands of the variety. 'SI 98' produces fewer seed heads than 'Sea Isle 2000' in side by side comparisons on golf courses.
5) The AFLP banding patterns obtained from duplicate DNA samples of 'SI 98' and 'Sea Isle 2000' illustrate significant differences in genomic structure. A primer combination of E-CA SEQ ID NO 1. and M-CAT SEQ ID NO 2, displays 30 bands, of which five, or 17%, are polymorphic between 'SI 98' and 'Sea Isle 2000'.

'SI 98' can be propagated asexually through springs, plugs, or sod. A single stolon of 'SI 98' was initially planted in soil-less media. Plant materials were continuously expanded vegetatively in a greenhouse until adequate quantities were available to establish field evaluation plots and eventually breeder and foundation blocks. All subsequent asexual reproductions of the 'SI 98' observed to date have been true to the original variety and remain true to type when asexually reproduced.

BRIEF DESCRIPTION OF THE PHOTOGRAPHS

FIG. 1 compares the appearance of flowering spike inflorescences of 'Sea Isle 1', 'Sea Isle 2000', and 'Sea Isle Supreme', 'Sea Isle Supreme' is the commercial name for 'SI 98'.

Figure 2:
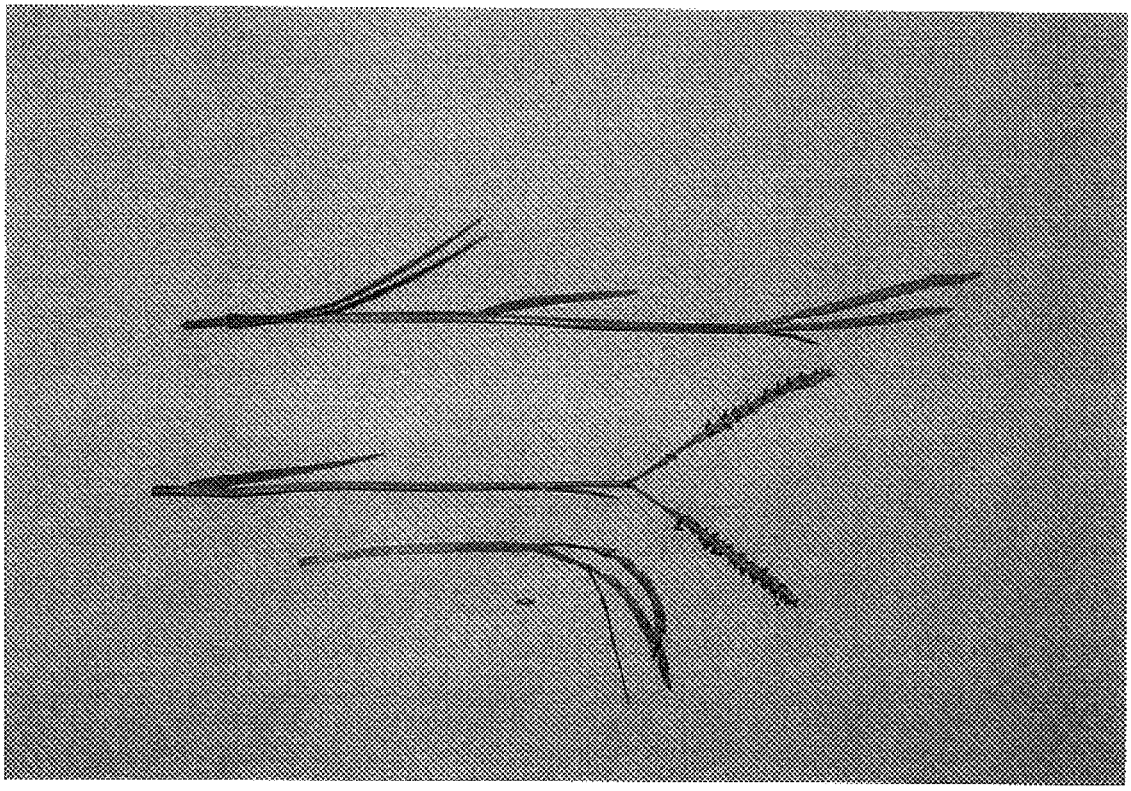

FIG. 2 shows the appearance of 'SI 98' inflorescence prior to anthesis, at anthesis, and at maturity.

Figure 3:
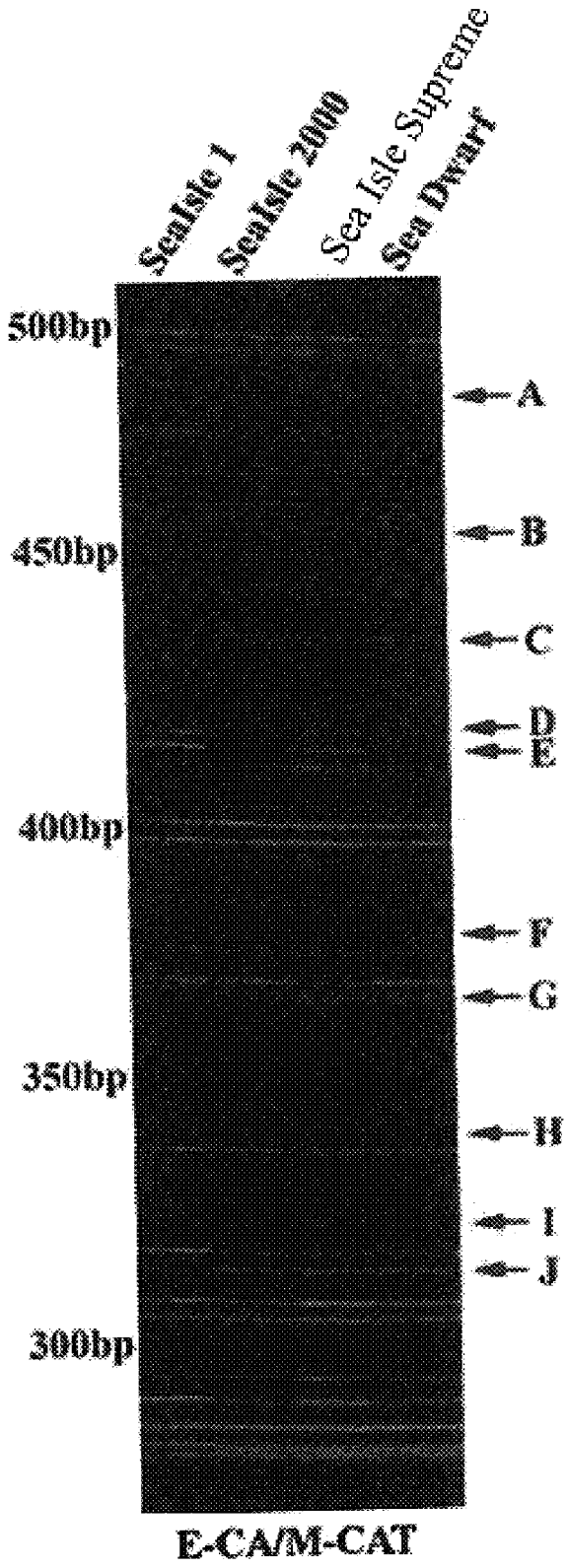

FIG. 3 compares the AFLP banding patterns obtained from DNA of 'Sea Isle Supreme' (the commercial name for 'SI 98') to three other patented and widely used cultivars, 'Sea Isle 1', 'Sea Isle 2000', and 'Sea Dwarf'. The primer combination of E-CA SEQ ID NO 1, and M-CAT SEQ ID NO 2. displays 30 bands, ten of which are polymorphic for these four varieties. Five bands are polymorphic between 'Sea Isle Supreme' and 'Sea Isle 2000', and two bands are specific for 'Sea Isle Supreme' within this random sample of the genome.

DETAILED BOTANICAL DESCRIPTION

Individual characteristics are given as means of 10 to 20 measurements, and colors are from the Royal Horticulture Society Colour Chart.

'SI 98' is a vigorous variety with semi-dwarf growth habit. It is low growing and spreads rapidly by producing large numbers of rhizomes and stolons. The mean height of the unmown canopy (culm height) is 19.4 cm, with a seed head exsertion height of 19.6 cm.

Flowering tillers:

The mean length and diameter of the peduncle is 86.3 mm and 0.7 mm.

The mean of the longest spike is 23.3 mm and there are two spikes per inflorescence.

The mean length of the spike branch from the flag leaf is 0.4 mm and the length and width of the blade on the flag leaf is 10.1 and 1.3 mm. The mean length of the sheath on the flag leaf is 31.3 mm.

The mean length and width of the blade of the $4^{th}$ leaf (the flag leaf is the $1^{st}$ leaf) is 36.5 mm and 2.5 mm, and the mean length of the sheath on the $4^{th}$ leaf is 12.1 mm.

The mean length of the $4^{th}$ internode is 8.4 mm. The color of the upper leaf surface is Green 137B and the lower leaf surface is Green 137C.

Anthers are 1.25 mm long and the glumes are glabrous. The anther color is Violet 86A, and stigma color is Violet 83A. Seeds which are very rarely produced in pure monostands due to self-incompatibility are 2.5 mm long and 1.5 mm wide and narrow in shape when produced by crossing with other widely diverse types.

Stolons:

The mean length and diameter of the $4^{th}$ intermode from the tip are 12.3 mm and 1.6 mm respectively.

The mean length and width of the $4^{th}$ leaf blade, at the $4^{th}$ node on stolon, are 5.6 mm and 2.0 mm respectively, with a leaf sheath 7.0 mm long.

The color of the stolon is Yellow-Green 146B.

'SI 98' is susceptible to dollar spot, a fungal disease that attacks many turf grasses in the humid Southeast US when nitrogen levels are maintained at low levels under turf conditions.

SEQUENCE LISTING

<160> NUMBER OF SEQ ID NOS: 2

<210> SEQ ID NO 1
<211> LENGTH: 18
<212> TYPE: DNA
<213> ORGANISM: Paspalum vaginatum O. Swartz

<400> SEQUENCE: 1 gactgcgtac caattcac 18

<210> SEQ ID NO 2
<211> LENGTH: 19
<212> TYPE: DNA
<213> ORGANISM: Paspalum vaginatum O. Swartz

<400> SEQUENCE: 2 gatgagtcct gagtaacat 19

I claim:

1. A new and distinct cultivar of seashore *paspalum* and plant named ‘SI 98’, substantially as herein illustrated and described.

* * * * *